United States Patent [19]
Tsao et al.

[11] Patent Number: 5,576,276
[45] Date of Patent: Nov. 19, 1996

[54] METHOD OF CLEANING OPHTHALMIC LENSES WITH ALKALINE COMPOSITION

[75] Inventors: Fu-Pao Tsao, Lawrenceville; Rosalind Dandridge, Doraville, both of Ga.

[73] Assignee: Ciba Geigy Corp., Tarrytown, N.Y.

[21] Appl. No.: 415,817

[22] Filed: Apr. 3, 1995

Related U.S. Application Data

[62] Division of Ser. No. 258,909, Jun. 13, 1994, which is a continuation of Ser. No. 993,500, Dec. 18, 1992, abandoned, which is a continuation of Ser. No. 748,603, Aug. 22, 1991, abandoned, which is a continuation of Ser. No. 451,488, Dec. 15, 1989, abandoned.

[51] Int. Cl.$^6$ ............................................. C11D 1/38
[52] U.S. Cl. ........................ 510/112; 252/175; 134/26; 134/42
[58] Field of Search ........................ 252/174.12, 175, 252/106, 174.23, DIG. 12

[56] References Cited

U.S. PATENT DOCUMENTS

| | | | |
|---|---|---|---|
| 3,910,296 | 10/1975 | Karageozian et al. | 134/2 |
| 3,954,644 | 5/1976 | Krezanoski et al. | 252/106 |
| 4,048,122 | 9/1977 | Sibley et al. | 252/541 |
| 4,126,587 | 11/1978 | Sibley et al. | 252/541 |
| 4,127,423 | 11/1978 | Rankin | 134/30 |
| 4,323,467 | 4/1982 | Fu | 252/106 |
| 4,490,389 | 12/1984 | Nelson et al. | 424/280 |
| 4,529,535 | 7/1985 | Sherman | 252/106 |
| 4,614,549 | 9/1986 | Ogunbiyi et al. | 134/19 |
| 4,748,189 | 5/1988 | Su et al. | 252/106 |
| 4,792,414 | 12/1988 | Su et al. | 252/174.17 |
| 4,812,173 | 3/1989 | Tsao et al. | 134/27 |
| 4,820,352 | 4/1989 | Riedhammer et al. | 252/174.21 |
| 4,863,627 | 9/1989 | Davies et al. | 252/105 |

FOREIGN PATENT DOCUMENTS

| | | |
|---|---|---|
| 124461 | 11/1985 | European Pat. Off. |
| 349487 | 1/1990 | European Pat. Off. |
| 139994 | 5/1990 | European Pat. Off. |
| 8605695 | 10/1986 | WIPO |

OTHER PUBLICATIONS

A M Gachon et al., Clin Chim Acta 129, (2), 189–95/1983).
T A Revina, et al, Med Paragital, Parazet, Bolenzi, 49(2), 33–5/1980).
C. Gelfi, et al, J. Biochem, Biophys. Methods 15(1), 41–8 (1987).

*Primary Examiner*—Jacqueline V. Howard
*Attorney, Agent, or Firm*—Edward McC. Roberts; R. Scott Meece; Michael U. Lee

[57] ABSTRACT

A pH controlled protein removal system and method in the substantial absence of (a) enzyme and (b) a surfactantly effective amount of a surfactant is disclosed. The method comprises contacting a substrate with a cleaning composition therefor, which compostion is substantially free of (a) enzyme and (b) surfactantly effective amount of a surfactant, for a period of time at an alkaline pH and removing said substrate from said composition.

15 Claims, No Drawings

METHOD OF CLEANING OPHTHALMIC LENSES WITH ALKALINE COMPOSITION

This is a divisional of Ser. No. 08/258,909, filed Jun. 13, 1994, which is a continuation of Ser. No. 07/993, 500, filed Dec. 18, 1992, now abandoned, which is a continuation of Ser. No. 07/748,603, filed Aug. 22, 1991, now abandoned which is a continuation of Ser. No. 07/451,488, filed Dec. 15, 1989, now abandoned.

FIELD OF THE INVENTION

The invention relates to the field of cleaning compositions, more specifically to cleaning compositions for the removal of protein from substrate, especially polymeric substrates and ophthalmic devices, specifically contact lenses.

BACKGROUND OF THE INVENTION

Cleaning compositions of various types have been known for many years, comprising many different components. Such composition are used to solubilize, abrade, oxidize, or reduce surfaces in an effort to remove undesirable surface adherents and restore a desired surface. Each type of surface to be cleaned presents its own characteristics which must be taken into account when choosing an appropriate cleaning composition therefor. Polymeric substrates offer particularly problematic issues in choice of cleanser composition due to the relatively large amounts of proteins which adhere thereto.

Especially thorny cleaning problems arise when the substrate to be cleaned is a contact lens. In addition to the parameters to be considered for the polymeric material of the contact lens per se, one must also take into account that the optical surfaces cannot be scarred, residue must be quickly and easily rinsed away with very small volumes of fluid, tonicity must be in an appropriate range so as not to destabilize the material, the cleaning system has to be non-toxic and non-allergenic (at least to the extent residue remains or is likely to remain) etc.

Specifically with reference to contact lens cleaning, protein adhesion and build up on the lens, sequestered primarily from tear fluid, has been a persistant and nagging problem. To deal with this difficulty, three general approaches have been attempted. The earliest attempt was to include an abrasive component, so that upon rubbing the lens therewith, the adhering protein would be broken up and town away from the lens. Compositions of this type include slurries of organic compounds such as sucrose, dextrose, etc., of inorganic compounds such as silica, sodium chloride, aluminum oxide, sodium carbonate, etc., of polymeric materials such as nylon beads, silicon polymer beads etc., or of other particulate matter such as glass beads.

A second type of attempted solution involved adding a surfactant. The surfactant is added to substantially solubilize the adherent protein. Compositions of this type include siloxane surfactants, alkylglycosides, polyalkylene oxy modified silicone etc. Attempts were also made in the combination of the two types above. Such compositions include Opticlean and Restore.

A third type of attempt to deal with the adherent protein has been to utilize an enzyme to digest the protein.

Of course the protein method can be used alone or in combination with any of the aforementioned methods of dealing with protein deposits. Typical available enzymatic cleaners for contact lenses include papain, subtilisin, pancreatin and other proteases.

While each of these methods has been somewhat successful in protein removal, each presents its share of drawbacks. For example, many abrasives are too harsh for use with contact lenses. Surfactants, in efficacious amounts for their surfactant properties, can irritate the eye terribly. Enzymes which degrade protein must never be placed into the eye for obvious reasons. Furthermore, the smaller protein fragments which result may be taken up further by the lens material or penetrate deeper into the lens matrix. In addition, enzymes if injected into the environment in substantial quantities create a considerable environmental hazard.

OBJECTS OF THE INVENTION

One object of the present invention is to provide a cleaner composition for use in the removal of protein from a substrate (i.e. contact lens) which avoids the problems of the art as noted above.

Another object of the invention is to provide a simple, yet effective cleaning regimen for contact lenses and other surfaces.

Still another object of the invention is to provide a means for creating a cleaning solution in accordance with the preceeding objectives in situ by the user thereof.

Yet another object is to provide an environmentally responsible formulation for removing protein from lenses.

SUMMARY OF THE INVENTION

Surprisingly, these and other objectives of the invention are achieved by a pH controlled cleaning compositions comprising water, a tonicity builder and a pH controller, in the substantial absence of (a) an enzyme and (b) protein dissolving efficacious amount of a surfactant and a method of removing protein therewith from a substrate having protein thereon comprising contacting said substrate with said composition for a time sufficient to loosen and remove substrate-adhered protein therefrom to result in a cleaned substrate and removing said substrate (absent the formerly adhered protein) from said composition.

DETAILED DESCRIPTION OF THE INVENTION

The invention in the case of a contact lens cleaner is directed to a solution having as its only requirements:

(a) water as a carrier;

(b) a tonicity builder in an amount sufficient to result in an approximately isotonic solution at the conclusion of the dosage regimen;

(c) a pH regulating agent capable of maintaining an alkaline pH in the range of 7.5 to 11.5 in the presence of the other components of the composition;

(d) substantially protein digesting enzyme; and (e) in the absence of a protein dissolving effective amount of a surfactant.

The tonicity builder can be any ionic or non-ionic species which is sufficiently soluble to give the appropriate tonicity, which after the cleaning regimen is complete is ocularly acceptable, and which is compatible with the lens material.

Typical tonicity builders for use in the invention include suitable water soluble salts compatible with ocular tissue, preferably alkali or alkali earth metal halide, sulfates, nitrates, carbonates, borates, and phosphates, more preferably sodium or potassium chloride. The tonicity builder is present in an amount sufficient to provide a tonicity in the final solution of the dosage regimen of 50 to 400 mosmole, most preferably 250 to 350 mosmole. When non-contact lens cleaning is the desired use, the tonicity builder may also be absent or in even greater amounts than set forth above.

The pH regulator maintains the pH preferably in the range of 7.5 to 11.5, more preferably 8.0 to 10.0, most preferably 8.5 to 9.5 for at least a period of time of from 10 min. to 24 hrs., preferably 30 min. to 8 hrs., more preferably 1 hr. to 6 hrs. or until a pH altering agent is added to the solution. The pH regulating agent is selected from inorganic or organic bases, preferably basic acetates, phosphates, borates, nitrates, sulfates, tartrates, lactates, carbonates, bicarbonates and mixtures thereof, more preferably basic phosphates, borates, citrates, tartrates, carbonates, bicarbonates and mixtures thereof. Typically, it is present in an amount of 0.001% to 2%, preferably 0.01% to 1%. The pH altering agent may or may not be a part of the initial composition and, when not part of the initial composition, may be added after a specified period of time as set forth above. The pH altering agent is preferably selected from inorganic or organic acids, more preferably acidic acetates, phosphates, borates, nitrates, sulfates, citrates, tartarates, lactates, carbonates, and bicarbonates, most preferably acidic phosphates, borates, citrates, tartarates, carbonates and mixtures thereof. The pH altering agent is present in an amount, when part of the original composition, or added in an amount, when not, which is sufficient to overcome the pH regulating agent and reset the pH to that desired.

Other typical and suitable ingredients, but not required ingredients include viscosity enhancer, defoaming agent, wetting agent and microbicidal agents.

As stated above, the inventive compositions do not contain any enzymes for the removal of protein. Additionally, the compositions of the present invention either contain no surfactants or, if they do, only amounts thereof which do not provide any significant protein dissolve property. The intent here is to allow inclusion of compounds which have multiple properties, one of which is as a surfactant in the composition. Such a compound is to be includable within the composition only at proportions which do not provide significant protein dissolving properties.

Enzyme, as used in the present context, is intended to mean a catalytic biological entity capable of degrading protein.

The compositions of the present invention can be formulated in nearly any conventional manner that would be considered suitable by those of ordinary skill.

Additional excipients typically used in protein removing cleaning compositions may be added depending on ultimate use compatibility. Such materials include viscosity enhancing agents, lubricants, abrasives, coating agents, disintegrating/dissoluting agent, binders, wetting agents, gildants, fillers, colors, etc. These additional materials are typically selected from dextrin, starch, sucrose, lactose, maltose, mannitol, sorbitol, dextrose, fructose, xylose, polyethylene glycol, polyethylene monostearates, glyceryl palmitostearate, stearic acid, magnesium stearate, calcium stearate, gelatin, polyvinyl pyrolidone, methylcellulose phthalate, polyethylene glycol. Amylose, alginic acid, effervescent systems ($CO_2$), sodium - starch glycolate, soy polysaccharides. Gelatin, guar gum, carboxymethylcellulose, hydroxyethylcellulose.

More specifically, the present invention is directed to the removal of protein, especially lysozyme (and other proteins typically adhering to contact lenses, such as IgM, serum IgA, secretory IgA, IgG, lactoferrin, albumin, peroxidase and tear specific prealbumin, from contact lenses, especially soft contact lenses. In the contact lens fields lysozyme (found in tear fluid), deposition on contact lenses and subsequent cleaning of lenses so fouled is a continuous and thorny problem. Most contact lenses have polymeric matrix structures which contain multiple negative sites at neutral or approximately neutral pH. Lysozyme, and a significant number of other proteins, has an isoelectric point above the usual range of pH in the cleaner used with contact lenses. Specifically, lysozyme has an isoelectric point of about 10–11. Below the isoelectric point, the protein has substantial positive charge and hence is attracted to the lens matrix. Enzymes, which cleave the protein into smaller pieces but do not account for the attractive ionic forces, only permit the fragment to permeate still further into the lens matrix, making cleaning even harder.

In the instant invention, the pH of the cleaner is maintained in the range of 7.5 to 11.5, which is near the isoelectric point. Since the lysozyme will have significantly less positive charge and may have a net negative charge the attractive force of the lysozyme for the lens will diminish or even be replaced by a weak repulsive force. In this way the protein contaminant on the lens can be readily removed.

In addition, the present invention offers advantages over the enzyme cleaners. First, the present invention does not fragment the adhered protein so that further migration of protein into the matrix is not increased. Additionally, as enzymes are themselves proteins, with the enzyme cleaners, there is risk of the lens having residual enzyme present even after careful rinsing. The present invention has no added enzyme and therefore is free of this problem. Still further, as enzymes continue to remain active after disposal, the present, enzyme free, formulations are much more environmentally elegant and suitable than prior enzyme containing compositions.

Still more specifically, the present invention is directed to compositions for cleaning protein deposits from contact lenses in the absence of enzymes and in the absence of a protein dissolving effective amount of a surfactant comprising a 250 to 350 mosmole solution at pH 7.5 to 11.5 by basic borate or phosphate buffer and sodium chloride.

In a further embodiment, a one step system is contemplated wherein an outer shell carries out the instant invention and a delayed release core adjusts the pH into a tolerable range from which the lens with minimal rinsing, can be placed directly on the users eye without significant irritation.

The invention method comprises contacting a proteinaccous deposit containing polymeric material, especially a contact lens, with a solution having a pH between about 7.5 and 11.5, preferably about 8.2 and about 10, more preferably about 8.5 to about 9.5, for a period of up to about 24 hours, preferably about 10 min. to about 12 hrs., more preferably 30 min. to about 8 hrs., most preferably 1 hr. to about 6 hrs., and removing the contact lens from such solution. If desired the so cleaned lens may then be rinsed or placed into a soaking solution. In further embodiment, the inventive solution is the result of a coating on a core dissolving and after a specified time in which the lens resides in such solution, the core dissolves, whereby the inventive solution is transformed in situ into a type of soaking solution. In such an embodiment, at minimum, the pH is returned to one from which with minimal rinsing direct administration to the eye would be suitable.

The instant invention will be more fully understood by reference to the following illustrative, but non-limiting Examples.

EXAMPLE 1

10 Vifilicon A lenses were soaked for 18–20 hrs. in 0.12% lysozyme solution containing 0.7% sodium chloride, 0.58% boric acid, and 0.05% sodium boratedecahydrate adjusted to pH 7.2 with dilute HCL a-dilute NaOH as needed, Lysozyme deposition was determined by absorbance measurement at 280 nm.

The lenses were then placed in one of 5 buffered saline solutions (as set forth in Table I) for 2 hours, rinsed in saline, and absorbance at 280 nm was measured again and is reported in Table I

TABLE I

| pH | 0.1 M sodium dihydrogen phosphate, mL | 0.1 M HCl, mL | 0.1 M NaOH, mL | 0.025 M borax, mL | Nacl | ABSORBANCE POST DEPOSITION | POST TREATEMENT | % DECREASE | AVERAGE % DECREASE |
|---|---|---|---|---|---|---|---|---|---|
| 6.0 | 50 | | 5.6 | | SUFFICIENT | 0.858 | 0.799 | 7 | 7 |
| | | | | | TO | 0.725 | 0.681 | 6 | |
| 7.0 | 50 | | 29.1 | | BRING | 0.826 | 0.740 | 10 | 8 |
| | | | | | TONICITY | 0.843 | 0.749 | 6 | |
| 8.0 | 50 | | 46.1 | | TO | 0.867 | 0.676 | 22 | 21 |
| | | | | | 300 | 0.828 | 0.670 | 19 | |
| 9.0 | | 4.6 | | 50 | MOSMOL | 0.842 | 0.696 | 17 | 15 |
| | | | | | | 0.799 | 0.707 | 12 | |
| 10.0 | | | 18.3 | 50 | | 0.708 | 0.540 | 24 | 21 |
| | | | | | | 0.881 | 0.733 | 17 | |

EXAMPLE 2 (COMPARATIVE)

The procedure of Example 1 is followed except that enzymatic cleaners designated in Table II, having the given pH values, after tablet dissolution were used instead of the present invention solution.

TABLE II

| Cleaner | Enzyme | pH | Absorbance Post Deposition | Post Treatment | % Decrease in Abs | Average % Decrease in Abs |
|---|---|---|---|---|---|---|
| Allergan ® Enzymatic Contact Lens Cleaner | Papain | 7.7 | 0.849 | 0.668 | 21 | 19 |
| | | 7.7 | 0.861 | 0.719 | 16 | |
| Alcon | Pancreatin | 6.3 | 0.825 | 0.715 | 13 | |
| Opti-Zyme ® Enzymatic Cleaner | | 6.4 | 0.848 | 0.647 | 24 | |
| Bausch * Lomb Renu ® Effervescent Enzymatic Contact Lens Cleaner | Subtilisin | 7.1 | 0.708 | 0.624 | 12 | |
| | | 7.1 | 0.892 | 0.740 | | |
| Allergan Ultrazyme ™ Enzymatic Cleaner (in saline) | Subtilisin A | 9.1 | 0.533 | 0.458 | | |
| | | 9.1 | 0.617 | 0.489 | | |

EXAMPLE III (COMPARATIVE)

The procedure of Example 1 is followed except that Bausch & Lombs ReNu Effervescent Enzymatic Cleaner containing the enzyme subtilisin is added to the instant invention solution, in the same concentration as in Example 2. This eliminates any confusion due to other materials in Example 2 which are dissimilar to those in Example 1. The results are shown in

TABLE III

| pH | Absorbance Post Deposition | Post Treatment | % Decrease in Abs | Average % Decrease in Abs |
|---|---|---|---|---|
| 6 | 0.750 | 0.677 | 10 | 8 |
| | 0.749 | 0.701 | 6 | |
| 7 | 0.828 | 0.763 | 8 | 10 |
| | 0.736 | 0.649 | 12 | |
| 8 | 0.674 | 0.608 | 10 | 13 |

TABLE III-continued

| pH | Absorbance Post Deposition | Post Treatment | % Decrease in Abs | Average % Decrease in Abs |
|---|---|---|---|---|
| 9 | 0.949 | 0.794 | 16 | 15 |
| | 0.582 | 0.514 | 12 | |
| | 0.961 | 0.785 | 18 | |

TABLE III-continued

| | Absorbance | | | Average |
|---|---|---|---|---|
| pH | Post Deposition | Post Treatment | % Decrease in Abs | % Decrease in Abs |
| 10 | 0.653 | 0.541 | 17 | 14 |
| | 0.700 | 0.629 | 10 | |

We claim:

1. A method of removing proteinaceous deposits from an ophthalmic lens, comprising the steps of:
   (a) contacting the contact lens an aqueous solution;
   (b) contacting said aqueous solution with a tonicity builder including a water soluble salt compatible with occular tissue; and
   (c) contacting said aqueous solution with a pH regulator, whereby the pH regulator maintains the pH of the aqueous solution contacting the lens from about 7.5 to 11.5 for a cleaning period of 10 minutes to 24 hours.

2. A method of claim 1, wherein said pH regulator is selected from the group consisting of basic acetates, phosphates, borates, nitrates, sulfates, tartrates, lactates, carbonates, bicarbonates, and mixtures thereof.

3. A method of claim 1, wherein the contacting occurs in the substantial absence of protein digesting enzyme and in the substantial absence of a surfactantly-effective amount of surfactant.

4. A method of claim 1, wherein the pH is maintained between 8.0 and 10.0 during the cleaning period.

5. A method of claim 4, wherein the pH is maintained between 8.5 and 9.5 during the cleaning period.

6. A method of claim 1, wherein the cleaning period is between one and six hours.

7. A method of claim 1, further comprising the step of neutralizing said high pH solution to a pH of about 6.5 to 7.5 after said cleaning period.

8. A method of removing proteinaceous deposits from an ophthalmic lens, comprising contacting said lens with a solution having a pH of 7.5 to 11.5 for a period of time sufficient to clean said lens.

9. A method of claim 8, wherein said solution pH is about 8.0 to 10.0.

10. A method of claim 9, wherein said solution pH is about 8.5 to 9.5.

11. A method of claim 9, wherein said period of time is 10 minutes to 24 hours.

12. A method of claim 9, wherein said period of time is one to six hours.

13. A method of claim 8, further comprising the step of neutralizing said high pH solution to a pH of about 6.5 to 7.5 after said cleaning period.

14. A method of cleaning ophthalmic lenses comprising contacting an ophthalmic lens with a solution having a pH of at least 8.5 for a period of time sufficient to clean the lens.

15. A method of claim 14, wherein the pH is between 8.5 and 11.5.

* * * * *